Figure 1:
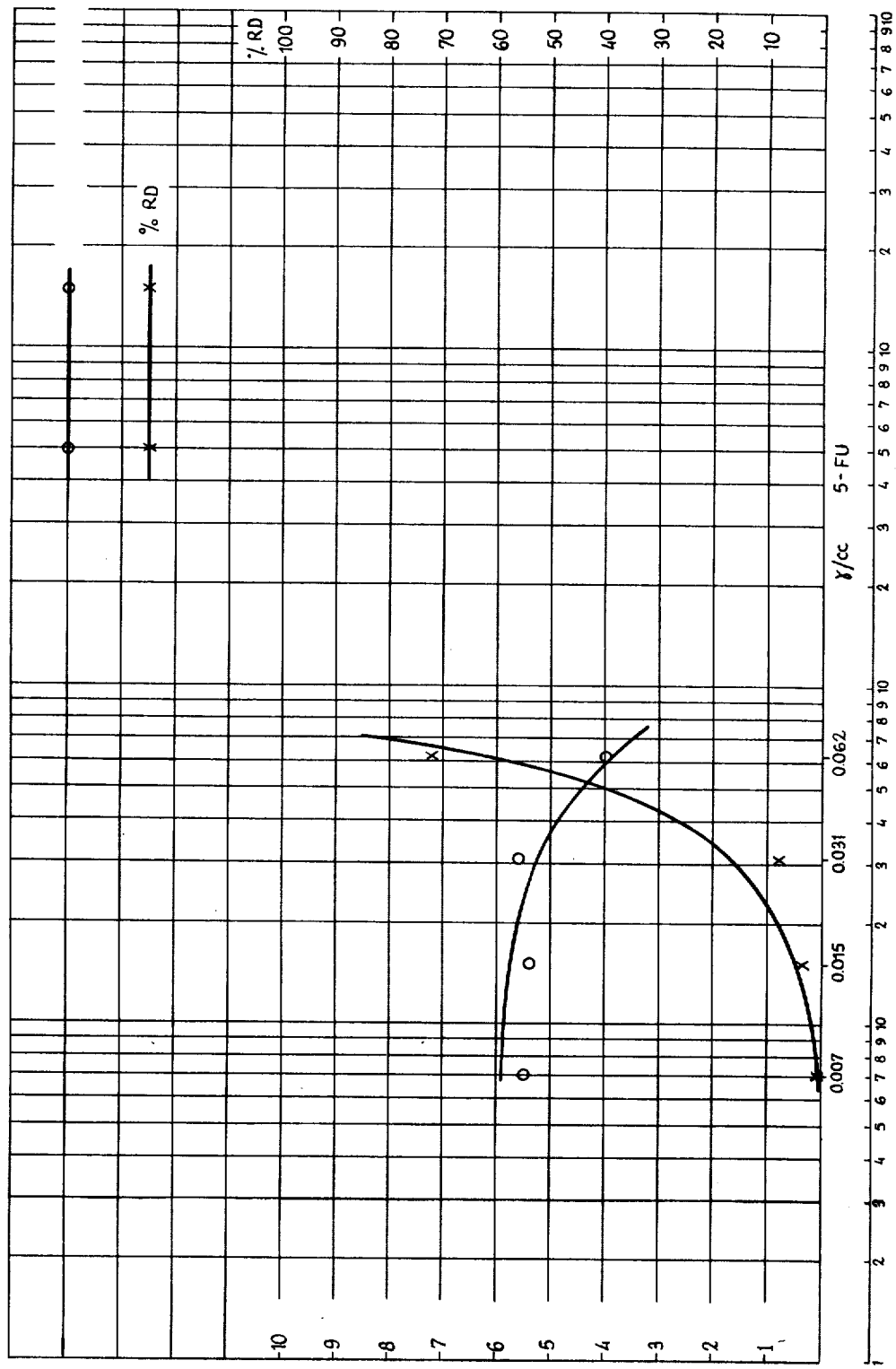

United States Patent [19]
Pacchetti et al.

[11] 3,954,536
[45] May 4, 1976

[54] PROCESS FOR MUTATING YEAST

[75] Inventors: Guido Pacchetti, Parma; Epifanio Bacchi, Manerbio (Brescia), both of Italy

[73] Assignee: Liquichimica S.p.A., Milan, Italy

[22] Filed: Mar. 19, 1975

[21] Appl. No.: 559,633

[30] Foreign Application Priority Data
Mar. 27, 1974 Italy.................................. 49767/74

[52] U.S. Cl.................................. 195/76; 195/97; 195/112; 426/60
[51] Int. Cl.² ........................................... C12K 1/02
[58] Field of Search ............ 195/112, 28 N, 82, 76, 195/79, 97

[56] References Cited
UNITED STATES PATENTS
3,298,923  1/1967  Banno et al......................... 195/112

OTHER PUBLICATIONS

Kakkar et al., "Induced Production of Lavender Mutants of Aspergillus Urguis by 5–Fluorouracil", Cited in Chemical Abstracts 78:92967.

Vanek et al., "Genetics of Industrial Microorganisms", Vol. II, Actinomycetes and Fungi, Elseiver Publishing Co., 1973, pp. 188–193.

Primary Examiner—David M. Naff
Assistant Examiner—R. B. Penland
Attorney, Agent, or Firm—Olson, Trexler, Wolters, Bushnell & Fosse, Ltd.

[57] ABSTRACT

Yeasts are mutated by treatment with 5-fluorouracil after growth in a medium containing glucose followed by growth in a medium containing glycerin.

5 Claims, 2 Drawing Figures

FIG. I

PROCESS FOR MUTATING YEAST

The present invention relates to a process for enriching with mutants of growth of microorganisms present in yeasts used for alimentary purposes. Several methods for the enrichment of mutants of growth of microorganisms have been already studied.

All methods proposed are based on the selective killing by numerous substances of the dividing yeast cells, subsequently to the fixation of the mutations induced by a mutagenic agent, after the cells have been put into conditions whereby only the non mutated cells can divide.

While, as far as, for instance, the bacteria are concerned, the problem has been effectively solved, by applying the method based on the selective elimination by the penicillin of the dividing cells, no likewise effective method exists which can be applied to the yeasts.

It has been found that the 5-fluoro-uracil (a specific mutagenic agent for the mithocondrial particles, called for conciseness 5-FU) acts selevtively on yeast cells in active division, not before at least 4 or 5 divisions occurred; therefore it is thereby to be considered as a substance suitable for being utilized in the enrichment of mutants of yeast growths as it removes all inconveniences due to the residual growth, anyway present, of the auxotroph mutants for the diffusion in the media of nutrilytes produced by the present prototrophs.

The process according to this invention consists of the stages as follows:

Stage 1: treatment with mutagenic agents;

2: passage in a rich media plus glucose for one generation;

This stage is rendered indispensable by the need of fixing the mutation, as the mutagenic agents having a structure analogous to that of the nucleic acids and of the type of the ionizing reactions (U V) induce with a high frequency alterations affecting only one of the two half-helixes forming the DNA (heteroduplex conditions). In order to fix the mutation it is indispensable that at least one replicative cycle will occur, allowing the mutation to segregate in homoduplex condition (both double helices mutated in the same pair of bases).

Stage 3: starvation;

Stage 4: passage to lean media containing 5-FU with glucose and without the aminoacid for which the auxotraph mutants are to be selected;

Stage 5: passage to starvation;

Stage 6: passage of the cells to rich media plus glycerin. In this stage only the cells not induced to RD (respiratory deficiency) will be capable of growing;

Stage 7: inoculation on rich media plus glycerin;

The stage 7 can replace the stage 6.

As it is known the enrichment in mutants, as related, is important for increasing the proteinic contents of the yeasts.

The effectiveness of the process according to this invention will be now illustrated with reference by way of example to the microorganism Saccharomyces Cerevisiae 5595/4c phe-met 4-1, located on different media in connection with the aspect to be evidenced.

The growth media will respond to the characteristics as follows:

1. M growth media: liquid rich media
2. 40 growth media: liquid lean media
3. M-Agar growth media: M media + Agar at 2%
4. 40-Agar growth media: 40 media + Agar at 2%

To the M and 40 media, as carbon source, glucose or glycerin will be added at the final 2% concentration.

To the 40 media if necessary will be added the aminoacids as necessary to the growth of the auxotroph cells at the final concentration of 20 mgr/cc.

The effect of the treatment on the yeast population will be evidenced by following the variations concerned with the main characteristics of the microorganisms as hereinafter reported:

1. curves of growth: The curves of growth are effected in rich and lean media suitably added with glucose or glycerin, with a starting inoculation of $5 \times 10^5$ cell/cc.

The culture will be incubated at 28°C on a reciprocating stirrer and at regular intervals tests on dishes will be effected on M-agar plus glucose in order to determine the vital titration and a count is effected with the globule counting chamber, in order to determine the total titration.

2. Survival curves: The survival curves in the starvation condition have been effected by re-suspending cells drawn from a cultur in logaritmic growth stage ($5 \times 10^7$ cell/cc) in lean media without aminoacids and without carbon sources. The suspension will be incubated at 28°C in reciprocating stirrer. At regular intervals an inoculation will be effected on M solid plus glucose. The dishes will be incubated at 28°C for three days and subsequently submitted to the test for the respiratory deficiency diagnosis.

3. Determination of the growth inhibiting minimum concentration (MIC). The MIC of 5-FU will be determined by suspending cells drawn from a logaritmic culture in 40 plus aminoacids plus glucose at the $1 \times 10^5$ cell/cc concentration in the presence of scalar concentrations of the substance. The cultures will be incubated at 28°C on a reciprocating stirrer and after 48 hours an optical analysis of turbidity of the cultures will be effected. The minimum 5-FU concentration inhibiting completely the growth is considered to be the MIC. Moreover for any concentration which at the turbidity analysis of the culture appears to be sub-inhibiting, an inoculation on M solid plus glucose is effected. After three days the growth colonies are submitted to diagnosis for the respiratory deficiency.

4. Mutagenesis with 5-FU on cells in the absence of division: the frequency of induction of deficient respiratory mutants (RD) with 5-FU in function of the time and in conditions of absence of division will be determined by treating with sub-MIC doses of 5-FU cells drawn from a culture in logaritmic stage at the $5 \times 10^7$ cell/cc concentration, in 40 minus aminoacid and with no carbon source. The suspensions are incubated at 28°C on a reciprocatory stirrer and at regular intervals inoculations will be effected on M solid plus glucose. The dishes are incubated at 28°C for 3 days and at the end the colonies as growth will be submitted to a respiratory deficiency diagnosis.

5. Diagnosis of the respiratory deficients (RD)

The diagnostic ascertainment of the RD has been effected by the TTC double layer method (2-3-5-triphenyltetrazol chloride) (Ogur and Nagai 1957). In each treatment M solid glycerin smears have been effected in parallel as a checking of the method.

6. Identification of auxotroph mutants.

The identification of auxotroph mutants is effected by a replication with velvet of colonies growth on dishes of M solid plus glycerin on 40 solid-glucose with no aminoacid.

The colonies which do not grow on 40 solid, are drawn again and retested by smearing.

In order to be capable of supplying a complete picture of the effectiveness of the process it is indispensable to characterize the single stages as far as the parameters as follows are concerned: generation times, survival and lesions induced in the mithocondrial particle. Furthermore, it is indispensable to have an isogenic prototroph strain and an isogenic auxotroph strain in order to avoid the variability deriving from different genetic sources. For the last cited purpose it has been considered suitable to have recourse to a prototroph obtained by reversal by an auxotroph strain. This has been obtained by inoculation on 40-solid plus glucose + phe of $10^7$ cells for dish of the 5595/4c phe-met 4-1.

The met + colonies insulated from these dishes, have been caused to grow in rich media plus glucose and subsequently located on dishes on 40 plus glucose. Therefrom, prototroph colonies have been insulated for both markers. Of the prototroph strains obtained by double reversal, the sole strain has been utilized which when tested in liquid culture, was not formed into clots; this strain has been denoted by R1. The process as aforesaid provides a growth stage in M plus glucose, indispensable for fixing the mutation and for a growing stage in M plus glycerin, indispensable for enrichment in mutants.

Table 1 shows the generation times of the 5595/4c and the R1 in the two conditions.

TABLE 1

| Media | 5595/4c | R1 |
|---|---|---|
| 40 + aminoacids | 3h . 30' | 2h . 48' |
| M + glucose | 2h . 12' | 2h . 12' |
| M + glycerin | 2h . 18' | 3h . 36' |

Under the same conditions, the frequency of the mutations to RD has been determined and shown in Table 2.

TABLE 2

| Media | 5595/4c %RD | R1 %RD |
|---|---|---|
| 40 + aminoacids | 1.5 – 2 | 1.5 – 2 |
| M + glucose | 1.5 – 2 | 1.5 – 2 |
| M + glycerin | 0.50 | 0.45 |

Also the two strains have been characterized as far as the survival is concerned in the starvation conditions in 40 without aminoacids and without carbon sources, in function of time.

Table 3 shows the values of the vital titration and of the induction to RD.

TABLE 3

| TIMES | 5595/4c VITAL TITRATION | %RD | R1 VITAL TITRATION | %RD |
|---|---|---|---|---|
| 0h | $1\times10^6$ | 1.5–2 | $1.1\times10^6$ | 1.5–2 |
| 6h | $1\times10^6$ | 0.5 | $1\times10^6$ | 0.5 |
| 13h | $1.3\times10^6$ | 0.5 | $1.3\times10^6$ | 0.5 |
| 25h | $9.5\times10^5$ | 0.5 | $1\times10^6$ | 0.5 |
| 63h | $9.5\times10^5$ | 0.5 | $1\times10^6$ | 0.5 |

As it will be remarked, the starvation condition, in the 63 hour period, is not lethal and does not seriously damage the mithocondrial particle. In the stage providing for the induction to RD only of the cells in active division, it is indispensable to establish what dose of 5-FU induces to RD with a high frequency the growing cells, and what effect it determines on the cytoplasmatic particle of cells which do not divide.

Figure 2:
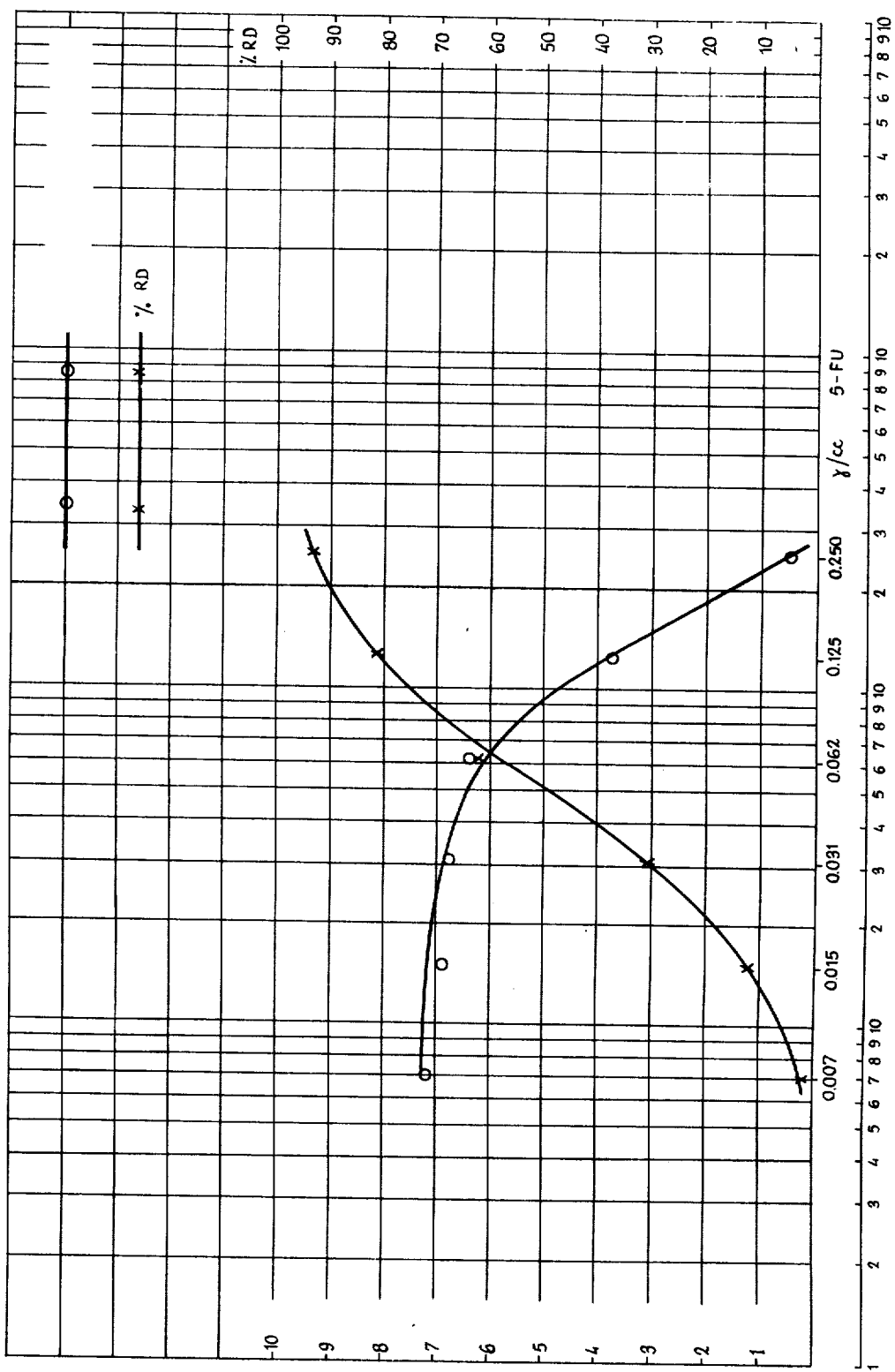

FIGS. 1 and 2 show the data of inhibition of the growth and of induction to RD, for the two strains in the presence of scalar concentrations of 5-FU.

Table 4 shows the survival data and of induction to RD for the two strains in non dividing conditions.

TABLE 4

| TIMES | 5595/4c VITAL TITRATION | %RD | R1 VITAL TITRATION | %RD |
|---|---|---|---|---|
| 0h | $4.2\times10^5$ | 1.5–2 | $8\times10^5$ | 1.5–2 |
| 13h | $4.4\times10^5$ | 0.5 | $9\times10^5$ | 0.5 |
| 24h | $4\times10^5$ | 0.5 | $8\times10^5$ | 0.5 |

As it is possible to note, the 5-FU acts exclusively on cells in active division.

As spectrum of dosages of 5-FU to be used in the treatment 0.060 γ/cc, 0.120 γ/cc, 0.180 γ/cc has been selected.

At these dosages, the two strains give a reply of an apparently exponential type for the induction to RD, and induction values are reached of the order of 80% with 10–20% of residual growth, as sufficient for causing 4–5 divisions to occur in a reasonable period of time.

EXAMPLE 1

A value of the mutation frequency for gene is assumed, of $10^{-7}$ per cell, for division. Taking into account that a treatment with nitrousguanidin, which is particularly effective mutagenic agent, raises the frequency of mutation per gene of three magnitudes, under particularly favourable conditions, have united pre-cultures of the 5595/4c strain and of the R1 strain in the ratios: $1:10^4$ with final concentrations of $10^7$ cell/cc. The data obtained in this first reconstruction test have been shown in Table 5.

As it is possible to note, the enrichment of auxotroph mutants is not such as to be defined satisfactory under the efficiency standpoint.

TABLE 5

| STAGES | VITAL TITRATION INITIAL | VITAL TITRATION FINAL | %RD | AUXOTROPH FREQUENCY OBTAINED | AUXOTROPH FREQUENCY EXPECTED |
|---|---|---|---|---|---|
| Growth in M plus glucose | $2\times10^7$ | $5\times10^7$ | 1.5–2 | $1\times10^{-4}$ | $1\times10^{-4}$ |
| 1 Starvation for 12ʰ | $4.5\times10^7$ | $3.02\times10^7$ | 0.5 | — | — |
| Treatment with 5-FU 0.060γ/cc, for 12ʰ | $5.6\times10^6$ | $5.2\times10^7$ | 58 | — | — |
| 2 Starvation for 12ʰ | $5\times10^7$ | $5.5\times10^7$ | 60.5 | — | — |
| Inoculation on M plus | | | | | |

TABLE 5-continued

| STAGES | VITAL TITRATION INITIAL | FINAL | %RD | AUXOTROPH FREQUENCY OBTAINED | EXPECTED |
|---|---|---|---|---|---|
| glycerin | — | $2.30 \times 10^7$ | — | $1.8 \times 10^{-4}$ | $2.5 \times 10^{-4}$ |

EXAMPLE 2

The effectiveness of the process of treatment with 5-FU, starvation, inoculation on M plus glycerin has been verified in the present example where a auxotroph to prototroph ratio of $1 : 10^2$ has been adopted.

Table 6 shows the data as obtained by using different dosages of 5-FU.

In this case the obtained enrichment is, as expected, at the dosage of $0.120$ γ/cc.

Greater and minor dosages have shown negative data.

Only the homozygous condition, in fact, can allow the development of recessive mutations in diploid cells. The so treated culture after a stage of growth in M media can be submitted to the subsequent treatments as provided by the process according to this invention.

The present invention has been described in one preferred embodiment being however understood that variations might be practically adopted without departing from the scope of the present industrial privilege.

Having thus described the present invention, what is claimed is:

1. A process for mutant enriching cultures of edible

TABLE 6

| STAGES | | VITAL TITRATION INITIAL | FINAL | %RD | AUXOTROPH FREQUENCY OBTAINED | EXPECTED |
|---|---|---|---|---|---|---|
| Growth on Glucose | | $5 \times 10^5$ | $1.3 \times 10^7$ | 1.5-2 | $1 \times 10^{-2}$ | $1 \times 10^{-2}$ |
| 1 Starvation for 12ʰ | | | | 0.5 | — | — |
| Treatment with 5-FU | 0.060γ/cc | $4.5 \times 10^6$ | $8 \times 10^7$ | 53.6 | | |
| | 0.120γ/cc | $4.3 \times 10^6$ | $5.76 \times 10^7$ | 71.0 | — | — |
| | 0.180γ/cc | $4.7 \times 10^6$ | $3.2 \times 10^7$ | 85.0 | | |
| 2 Starvation for 12ʰ | 0.060γ/cc | $8 \times 10^7$ | $8.4 \times 10^7$ | 54.3 | | |
| | 0.120γ/cc | $7.1 \times 10^7$ | $7.4 \times 10^7$ | 73.8 | — | — |
| | 0.180γ/cc | $3.2 \times 10^7$ | $2 \times 10^7$ | 89.3 | | |
| Inoculation on M | 0.060γ/cc | — | $3.2 \times 10^7$ | — | $5 \times 10^{-3}$ | $2.1 \times 10^{-2}$ |
| plus glucose | 0.120γ/cc | — | $1.6 \times 10^7$ | — | $3.4 \times 10^{-2}$ | $4 \times 10^{-2}$ |
| | 0.180γ/cc | — | $2.3 \times 10^6$ | — | $4.7 \times 10^{-2}$ | $1 \times 10^{-1}$ |

On the grounds of the obtained results it is possible to conclude that the process according to this invention for the enrichment of mutants in growths of yeasts, proved to be effective.

The extension of this experimental process to other species can be made after their characterization as far as the response to the treatment with 5-FU under the conditions of active division and of non division is concerned.

Also the problem of insulating the mutants in diplont species (lacking of a stable haploid phase) can be solved by applying the proposed process, with the variant to be introduced between the stage two (growth in media M plus glucose) and the stage 3 (starvation).

In this case it is indispensable to submit the cells to a treatment with agents increasing the frequency of somatic re-combination (f.i. irradiating the culture with U V).

This treatment is indispensable for causing the mutations induced by the mutagenic agent in one of the components the pair of determinants genetic whereby it is wanted to select the mutant will be fixed in a homozygous condition.

yeasts comprising treating the cultures with 5-fluoro-uracil, said treatment with 5-fluoro-uracil being effected after a growth stage in rich media plus glucose and being followed by a growth stage in rich media plus glycerin.

2. A process as claimed in claim 1 consisting of the stages as follows: treatment with mutagenic agents; fixing the mutation in rich media plus glucose for one generation; starvation; treatment in lean media containing 5-fluoro-uracil with glucose; starvation; treatment in rich media plus glycerin; inoculation on rich media plus glycerin.

3. A process as claimed in claim 2, wherein use is made of doses of 5-fluoro-uracil variable from 0.060 γ/cc to 0.180 γ/cc.

4. A process as claimed in claim 2, wherein the time of treatment varies from one to 64 hours.

5. A process as claimed in claim 2, applied to insulating mutants in diplonts species, wherein between the stage of growth in rich media plus glucose and the subsequent starvation stage, the cells are submitted to a treatment with an agent effective to increase the frequency of somatic recombination.

* * * * *